United States Patent
Zheng et al.

(10) Patent No.: US 12,215,342 B2
(45) Date of Patent: Feb. 4, 2025

(54) METHOD FOR PREPARING PEI-LIPID NANOPARTICLES USED FOR DELIVERING A MRNA VACCINE AND TRANSFECTING STEM CELLS

(71) Applicants: Healthina Stem Cell Industry Platform (Tianjin) Limited, Tianjin (CN); Tangyi Holdings(Shenzhen) Limited, Shenzhen (CN)

(72) Inventors: Bin Zheng, Tianjin (CN); Yulin Cao, Beijing (CN); Tingting Hua, Tianjin (CN); Shixiang Cheng, Tianjin (CN)

(73) Assignees: Healthina Stem Cell Industry Platform (Tianjin) Limited (CN); Tangyi Holdings(Shenzhen) Limited (CN)

( * ) Notice: Subject to any disclaimer, the term of this patent is extended or adjusted under 35 U.S.C. 154(b) by 192 days.

(21) Appl. No.: 17/862,421

(22) Filed: Jul. 12, 2022

(65) Prior Publication Data

US 2023/0272426 A1 Aug. 31, 2023

(30) Foreign Application Priority Data

Feb. 28, 2022 (CN) .......................... 202210189584.6

(51) Int. Cl.
    *C12N 15/88* (2006.01)
    *A61K 9/127* (2006.01)
    *A61K 9/51* (2006.01)

(52) U.S. Cl.
    CPC ............ *C12N 15/88* (2013.01); *A61K 9/1272* (2013.01); *A61K 9/5123* (2013.01)

(58) Field of Classification Search
    CPC ..... C12N 15/88; A61K 9/1272; A61K 9/5123
    See application file for complete search history.

(56) References Cited

U.S. PATENT DOCUMENTS

2018/0161272 A1* 6/2018 Obaid ..................... A61K 9/127
2020/0206134 A1* 7/2020 Kalinichenko ......... A61P 11/00
2021/0330600 A1* 10/2021 Talukder ................ A61K 39/00

FOREIGN PATENT DOCUMENTS

WO WO-2009129354 A2 * 10/2009 ........... B01D 61/002

OTHER PUBLICATIONS

BroadPharm: A Worldwide Leading PEG Supplier. What is a helper lipid? (Year: 2022).*
G-Biosciences: Water, Endotoxin Free (Year: 2019).*
Warriner et al. Biomacromolecules 2018 19 (11), 4348-4357 (published: Oct. 24, 2018) and (Year: 2018).*
Mali et al. J Appl Polym Sci 2021, 138(45), e51323 (published: Jun. 2, 2021). (Year: 2021).*

* cited by examiner

*Primary Examiner* — Genevieve S Alley

(57) ABSTRACT

The method of preparing polyethyleneimine-lipid nanoparticles (PEI-LNPs) for transfecting stem cells includes the following steps: S1, adding anhydride to a PEI solution to produce polycarboxylic acid; S2, dissolving the PEI-LNPs from S1, together with DPPC, DPPG, DPPE-PEG-COOH and cholesterol in chloroform, dissolving cGAMP in a water and then adding to such chloroform solution, and performing vacuum evaporation to remove the chloroform; S3, adding PBS for hydration, and performing ultrasonication to obtain liposomes; and S4, adding EDC/NHS to the liposome solution obtained for reaction for 15 min, then adding mRNA, and stirring the mixed solution to obtain a bionic virus nanovaccine. The prepared PEI-LNPs are used for delivering an mRNA vaccine and transfecting stem cells, wherein through a lipid PEI derivative library synthesized based on short-branched PEI with a variable length and hydrophobic tail substitution ratio, short-branched PEI can form a stable complex with the mRNA vaccine.

6 Claims, 3 Drawing Sheets

METHOD FOR PREPARING PEI-LIPID NANOPARTICLES USED FOR DELIVERING A MRNA VACCINE AND TRANSFECTING STEM CELLS

CROSS REFERENCE TO THE RELATED APPLICATIONS

This application is based upon and claims priority to Chinese Patent Application No. 202210189584.6, filed on Feb. 28, 2022, the entire contents of which are incorporated herein by reference.

TECHNICAL FIELD

The present invention relates to the technical field of lipid nanoparticles (LNPs), specifically a nucleic acid delivery system containing lipid nanoparticles which can deliver an mRNA vaccine and transfect stem cells. In particular, the invention relates to a method for preparing PEI-LNPs used for delivering an mRNA vaccine and transfecting stem cells.

BACKGROUND

At present, stem cells play an increasingly important role in the basic research and clinical application of life sciences, and have a very broad application prospect in cell therapy, tissue and organ repair, developmental biology, pharmacology and other fields. The stem cells have the potential for genetic manipulation that controls stem cell behaviors and guides stem cells to differentiate into a variety of tissue-specific cell types, such as cardiomyocytes, neurons, beta cells, platelets and red blood cells, leading to a clinical application of stem cells for therapy of myocardial injury, spinal cord injury, autoimmune diseases, etc. Stem cell therapy features a variety of advantages, such as hypotoxicity (or nontoxicity). Even if the exact pathogenesis of the disease is not fully understood, a better therapeutic effect can be achieved. Autologous stem cell transplantation (ASCT) can avoid an immunological rejection and is surprisingly effective in treating diseases for which traditional therapies have failed.

Genetic manipulation tools of stem cells rely on nucleic acids and proteins. However, the stem cells are considered difficult to transfect, and the options for importing nucleic acids into stem cells remain limited. Most commercially available products, such as liposomes and FuGENE® transfection agents, have a DNA transfection efficiency of less than 20%. At present, vaccine therapies based on mRNA (messenger RNA) antigens are gradually applied. Not only mRNA antigens can achieve a rapid protein expression in non-dividing and difficult-to-transfect cells such as stem cells, but their immunogenicity can be regulated by chemical modification.

mRNA-based vaccines feature a high efficiency, rapid speed, high safety, low preparation cost, etc., so they have greater development potential and advantages compared with vaccines based on protein short peptide and plasmid DNA. At present, in many basic researches and clinical trials, intracellular delivery of mRNA vaccines has been shown to induce the synthesis, processing and presentation of coded antigen proteins and to activate T cells, thus playing an effective role in anti-tumor immune response.

An injection of naked mRNA without modification and delivery carrier features a fast speed and low cost. However, due to the high negative charge, easy degradation and poor stability of mRNA, in vivo delivery of mRNA still faces potential challenges. Tools for delivering mRNA and plasmid DNA to a human body require high efficiency and safety. In currently available transport tools, long linear polyethyleneimine (PEI) has been successfully applied in cell transfection in vitro and in vivo. However, short-branched PEI is less efficient than long linear PEI. Due to large sizes of long circular plasmids, the short-branched PEI could not form stable complexes. In addition to polymer delivery tools, LNPs have been developed for high-efficiency hepatocyte transfection in vivo and have been verified in clinical trials. However, DLin-MC3-DMA-based LNPs require multi-step synthesis such as group covering and over-purification, which severely limits the possibility of LNPs for rapid structural optimization in stem cell transfection.

SUMMARY

The present invention is intended to provide a method for preparing PEI-LNPs used for delivering an mRNA vaccine and transfecting stem cells. Through a lipid PEI derivative library synthesized based on short-branched PEI with a variable length and hydrophobic tail substitution ratio, short-branched PEI forms a stable complex, and plasmid DNA is delivered to stem cells, so as to improve effectiveness and safety of stem cell transfection.

To achieve the aforesaid purposes, the present invention provides a method for preparing PEI-LNPs used for transfecting stem cells, including the following specific steps:

S1, adding anhydride to a PEI solution to produce PEI-LNPs and polycarboxylic acid;

S2, dissolving the PEI-LNPs obtained in S1, together with dipalmitoyl phosphatidylcholine (DPPC), dipalmitoyl phosphatidylglycerole (DPPG), Dipalmitoyl phosphatidylethanolamine-polyethylene glycol-COOH (DPPE-PEG-COOH) and cholesterol in chloroform, dissolving cGAMP in a sterile water and then adding it to the chloroform solution, and performing vacuum evaporation to remove the chloroform after performing vacuum ultrasonication for 30 min;

S3, adding PBS for hydration, and then performing ultrasonication for 20 min to obtain liposomes; and S4, adding EDC/NHS to the liposome solution obtained in S3 and let stand for reaction for 15 min, then adding mRNA, and stirring the mixed solution at a room temperature for 1 h to obtain a bionic virus nanovaccine.

Preferably, the method includes the following specific steps:

S1, adding anhydride to a PEI solution to produce PEI-LNPs and polycarboxylic acid;

S2, dissolving the PEI-LNPs obtained in S1, together with 13 μg of DPPC, 2 μg of DPPG, 2 μg of DPPE-PEG-COOH and 1 μg of cholesterol in 3 mL of chloroform, dissolving cGAMP in 1 mL of DNase/RNase-free water and then adding it to the chloroform solution, and performing vacuum evaporation to remove the chloroform after vacuum ultrasonication for 30 min;

S3, adding 2 mL of PBS for hydration, and then performing ultrasonication for 20 min to obtain liposomes; and S4, adding EDC (10 mg/mL)/NHS (10 mg/mL) to the liposome solution obtained for reaction for 15 min, and then adding mRNA, wherein a volume ratio of mRNA: liposomes is 2:1; stirring the mixed solution at a room temperature for 1 h to obtain a bionic virus nanovaccine.

Preferably, in S1, the anhydride is C8-C18 alkyl anhydride.

Preferably, in S1, a mass ratio of PEI-LNPs/anhydride is 1:0.5, and that of PEI-lipid/plasmid is 1:1.

Preferably, the anhydride is C12 alkyl anhydride.

Preferably, in S4, the mRNA vaccine has the following synthesis process:

(1) dissolving liposomes in chloroform, then adding an mRNA aqueous solution to such mixed solution, and performing ultrasonication for 15 min and vacuum evaporation; and (2) adding PBS for hydration to obtain an mRNA vaccine.

Preferably, in S(1), the liposomes are composed of 50% of ionogenic cationic lipid Dlin-MC3-DMA, 10% of DSPC, 35% of cholesterol and 5% of DPPE-PEG.

Preferably, the present invention further provides an application of the PEI-LNPs in delivering an mRNA nanovaccine and transfecting stem cells (such as HESC).

Therefore, the present invention adopts the method for preparing PEI-LNPs used for delivering an mRNA vaccine and transfecting stem cells, which provides a simple method to generate a PEI-LNPs library with neutralized charge for delivering an mRNA vaccine and transfecting stem cells, by making full use of the characteristics of PEI-LNPs combining with polymers and lipids.

LNPs of the present invention are based on small-branched PEI and lipid anhydride. More than 15% of LNPs exhibit a high transfection efficiency in different cell types, and a length and ratio of hydrophobic alkyl substitution are the key parameters for efficient gene delivery. More importantly, a transfection efficiency of improved PEI is higher than that of original cation PEI. Improved PEI shows that efficient plasmid DNA delivery can effectively co-transfer two plasmid DNAs into difficult-to-transfect human embryonic stem cell (HESC). More than 20 lipid PEIs are synthesized, and mRNA vaccine delivery is tested in different cell types, including HESC.

The present invention features the following specific technical effects:

(1) The LNPs of the present invention can be used to deliver an mRNA vaccine and transfect stem cells, and can improve an efficiency and safety of delivering an mRNA vaccine and transfecting stem cells.

(2) According to a simple modular and extensible method used for nucleophilic reaction between PEI and anhydride of the present invention, a lipid PEI derivative library is synthesized in parallel based on short-branched PEI with a variable length and hydrophobic tail substitution ratio, and a part of charge of the synthesized PEI lipids is neutralized, which can potentially reduce toxicity of amidogen in PEI.

(3) According to the PEI-LNPs of the present invention, the preparation method is simple, convenient to operate, modular, extensible, easy to translate and deliver mRNA and transfect stem cells, highly safe, and suitable for promotion, without needing high technical requirements.

The technical solutions of the present invention will be further described below in detail in combination with the accompanying drawings and embodiments.

DETAILED DESCRIPTION OF THE EMBODIMENTS

Figure 1:
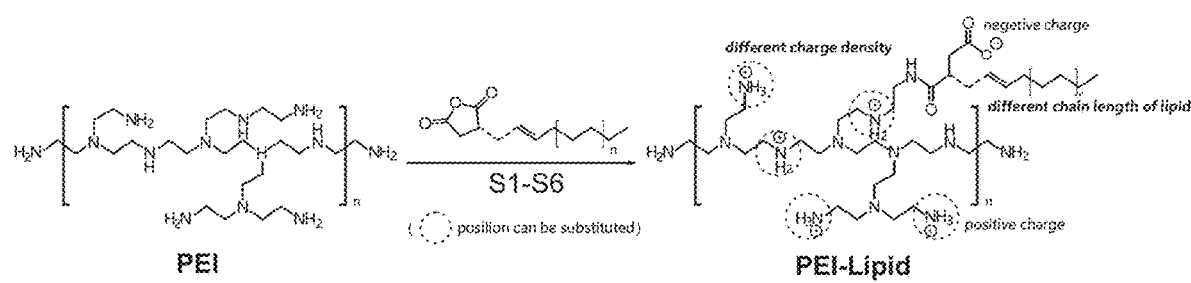
FIG. 1 shows a synthesis route for producing PEI-LNPs.
Figure 2:
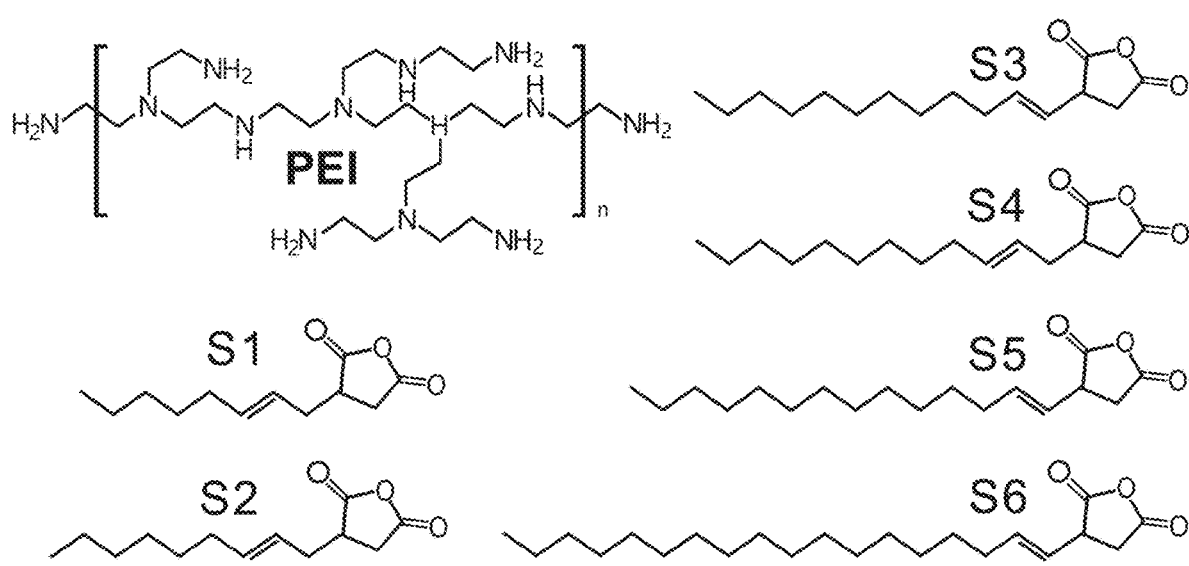
FIG. 2 shows a chemical formula of a PEI and anhydrides for producing PEI-LNPs.
Figure 3:
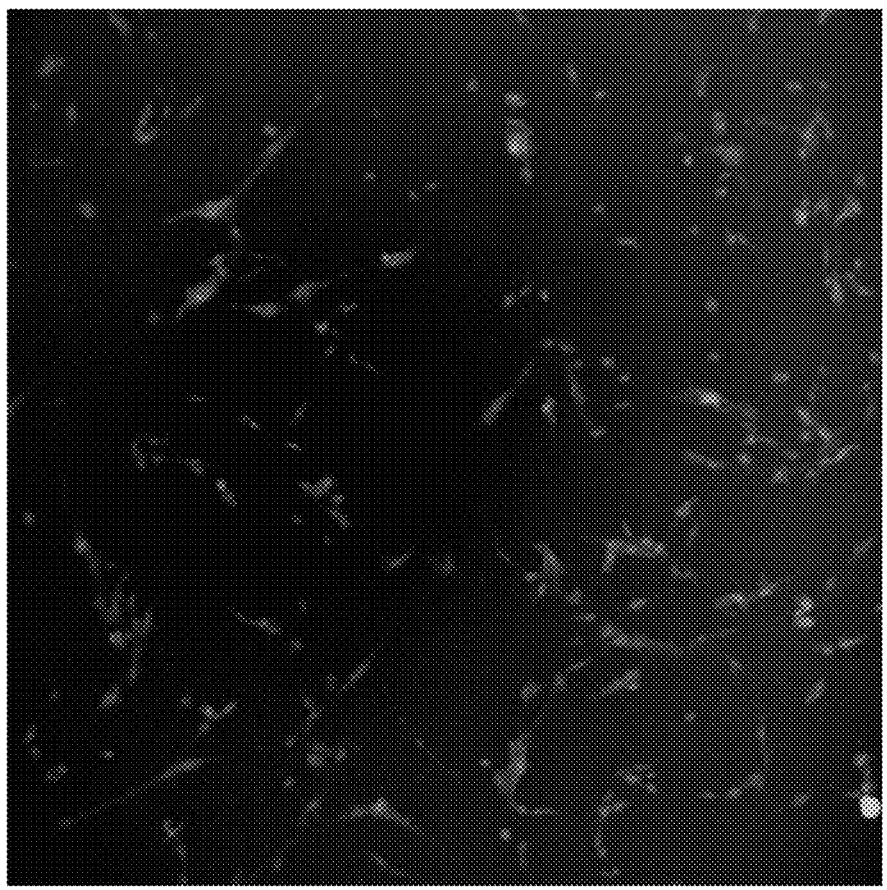
FIG. 3 shows fluorescence imaging of PEI-LNPs successfully delivering an mRNA nanovaccine.

The technical solutions of the present invention will be further described below in combination with the accompanying drawings and embodiments.

Unless otherwise defined, the technical or scientific terms used herein should have ordinary meanings understood by those of ordinary skill in the art reading the present invention.

It is apparent to those skilled in the art that the present invention is not limited to the details of the above-mentioned exemplary embodiments and can be realized in other specific forms without departing from the intention or essential features of the present invention. Therefore, in all respects, the embodiments should be considered to be exemplary and non-restrictive. The scope of the present invention is limited by the appended claims rather than the above-mentioned description, so that all changes falling within the meaning and scope of the equivalents of the claims are intended to be included in the present invention, and any accompanying drawing marks in the claims should not be deemed to limit the claims involved.

Moreover, it should be understood that although the specification is described according to the implementation modes, not each implementation mode contains only one independent technical solution. This narrative form of the specification is for the sake of clarity only. Those skilled in the art should take the specification as a whole, and the technical solutions in various embodiments may be combined appropriately to form other implementation modes that can be understood by those skilled in the art. These other implementation modes should also fall within the protection scope of the present invention.

In addition, it should be understood that the above-mentioned specific embodiments are used for explaining the present invention only, and the protection scope of the present invention is not limited to such specific embodiments. Within the technical scope disclosed by the present invention, the equivalent substitutions or changes made by those skilled in the art based on the technical solutions and inventive concept of the present invention should fall within the protection scope of the present invention/invention.

The "including/comprising" or "containing" and similar words used herein refer to that the element ahead of the word covers the elements listed behind the word and does not exclude the possibility of covering other elements as well. The orientations or position relations indicated by terms "inside", "outside", "up" and "down" are those shown based on the accompanying drawings, only used for the convenience of describing the present invention and simplifying the description, rather than indicating or implying that the device or element referred to must have a particular orientation or be constructed and operated in a particular orientation, so they cannot be understood as a limitation to the present invention. When the absolute position of the object described changes, the relative position relation may also change accordingly. In the present invention, unless otherwise expressly specified and limited, the term "attaching" should be understood in a broad sense. For example, two elements may be connected fixedly, connected detachably, or integrated; two elements may be connected directly, or connected indirectly through an intermediate medium, or communicated internally or interact. Those of ordinary skill in the art can understand the specific meanings of such terms in the present invention according to the specific situations. The term "about" used herein has the meaning known to those skilled in the art, and preferably refers to that the value modified by the term is within the range of ±50%, ±40%, ±30%, ±20%, ±10%, ±5% or ±1%.

All terms (including technical or scientific terms) used in the disclosure have the same meanings as those understood by those of ordinary skill in the art of the disclosure, unless otherwise specifically defined. Moreover, it should be understood that terms defined in a general dictionary should be understood to have meanings consistent with those in the context of the relevant techniques, and should not be interpreted in an idealized or highly formal sense, unless expressly defined herein.

The techniques, methods and equipment known to those of ordinary skill in the art may not be discussed in detail, but where appropriate, such techniques, methods and equipment should be considered as a part of the specification.

The contents disclosed in the prior art literature referenced in the specification of the present invention are incorporated herein by reference in its entirety.

EXAMPLES (I) Materials and Instruments

Branched PEI (PEI, mean Mw ~800, mean Mn ~600): Purchased from Hong Kong SigmaAldrich Co., Ltd.; octaethyl succinic anhydride (S1, cis-trans mixture, GC>95.0%), (2-pelargonic-1-base) succinic anhydride (S2, branched isomer mixture, >90%), tetrapropylsuccinic anhydride (S3, branched isomer mixture, >85%), 2-dodecyl succinic anhydride (S4, cis and trans mixture, >95%), and tetradecenyl succinic anhydride (S5, >85% GC): Purchased from Shanghai TCI Development Co., Ltd.; solvents: Purchased from China Beauty Yale (Shanghai) Chemical Technology Co., Ltd. Reagents were not further purified for use, unless otherwise stated. Solvents were purchased from China Beauty Yale (Shanghai) Chemical Technology Co., Ltd.

(II) Preliminary Synthesis of a PEI-Lipid Library

Each LNP was derived from a PEI-LNP library with different structure that was reacted and generated by a PEI solution and an anhydride solution.

In order to prepare a PEI-lipid library with neutralized charge, a parallel synthesis of branched PEI (mean Mw ~800) was performed at different concentrations (10%-40%) by six different anhydrides S1-56 (alkyl chain lengths were C8-C18, with a chemical formula as shown in FIG. 1B). A synthesis of PEI derivatives was based on a reaction between anhydrides S1-S6 and PEI (a ratio of both was 10%-40%), and 24 kinds of amides PS11-PS64 (as shown in Table 1) were generated according to a nucleophilic reaction. The reaction was efficient, simple, and completed in just one day. The PEI-LNP library with different composite structures for rapid modularization was used for gene delivery.

TABLE 1

Comparison Table of Examples of PEI-LNPs

|  | S1 | S2 | S3 | S4 | S5 | S6 |
|---|---|---|---|---|---|---|
| 10% | PS11 | PS21 | PS31 | PS41 | PS51 | PS61 |
| 20% | PS12 | PS22 | PS32 | PS42 | PS52 | PS62 |

TABLE 1-continued

Comparison Table of Examples of PEI-LNPs

|  | S1 | S2 | S3 | S4 | S5 | S6 |
|---|---|---|---|---|---|---|
| 30% | PS13 | PS23 | PS33 | PS43 | PS53 | PS63 |
| 40% | PS14 | PS24 | PS34 | PS44 | PS54 | PS64 |

Screening of an efficiency of delivering an mRNA nanovaccine was performed by a one-step method. After Hela cells were inoculated to a 96-orifice plate for 12 h, the PEI-LNPs were transferred to culture holes. After culture for 2 d, cell nucleus Hoechst staining and fluorescence microscope imaging analysis were performed.

Commercialized lipo2000 was taken as positive control. The results show that more than 80% of lipids in the library exhibited green fluorescent protein (GFP) positive, and more than 15% of lipids exhibited a transfection efficiency apparently higher than lipo2000. Many gene delivery reagents with high transfection efficiency can be efficiently synthesized by a combined chemical method.

(III) PEI-LNPs of PS00-PS64 were prepared according to the following general process, including the following steps:

A PEI-based library synthesis included a preparation of a PEI solution and an anhydride solution. Then anhydrides S1-S6 were added to a PEI solution, the mixture was reacted for 24 h at 50° C., and a reaction product was synthesized for gene delivery and screening.

TABLE 2

Preparation of Control Samples and Preparation Examples PS00-PS64

| Example | Anhydride | Ratio of PEI to Anhydride | Example | Anhydride | Ratio of PEI to Anhydride |
|---|---|---|---|---|---|
| PS00 | None | None | — | — | — |
| PS11 | S1 | 10% | PS12 | S1 | 20% |
| PS21 | S2 | 10% | PS22 | S2 | 20% |
| PS31 | S3 | 10% | PS32 | S3 | 20% |
| PS41 | S4 | 10% | PS42 | S4 | 20% |
| PS51 | S5 | 10% | PS52 | S5 | 20% |
| PS61 | S6 | 10% | PS62 | S6 | 20% |
| PS13 | S1 | 30% | PS14 | S1 | 40% |
| PS23 | S2 | 30% | PS24 | S2 | 40% |
| PS33 | S3 | 30% | PS34 | S3 | 40% |
| PS43 | S4 | 30% | PS44 | S4 | 40% |
| PS53 | S5 | 30% | PS54 | S5 | 40% |
| PS63 | S6 | 30% | PS64 | S6 | 40% |

Different anhydride and PEI at different ratios were prepared to PEI-LNPs, as shown in Table 2. These different PEI-LNPs delivered an mRNA vaccine so that stem cells exhibited GFP, and an expression efficiency was determined by calculating a ratio of fluorescence to total cells after different PEI lipids delivered the mRNA vaccine. The measurement results are as shown in Table 3.

TABLE 3 mRNA Vaccine Delivery Efficiency of Control Samples and Preparation Examples

| Example | mRNA Vaccine Delivery Efficiency | Example | mRNA Vaccine Delivery Efficiency |
|---|---|---|---|
| PS00 | 0 | Lipo2000 | 1.1 |
| PS11 | 0.25 | PS12 | 0.02 |
| PS21 | 0.1 | PS22 | 0.45 |

TABLE 3-continued mRNA Vaccine Delivery Efficiency of Control
Samples and Preparation Examples

| Example | mRNA Vaccine Delivery Efficiency | Example | mRNA Vaccine Delivery Efficiency |
|---|---|---|---|
| PS31 | 1.7 | PS32 | 2.1 |
| PS41 | 0.22 | PS42 | 0.3 |
| PS51 | 0.06 | PS52 | 0.7 |
| PS61 | 0.04 | PS62 | 0.2 |
| PS13 | 0.4 | PS14 | 0.75 |
| PS23 | 0.55 | PS24 | 1.2 |
| PS33 | 1.35 | PS34 | 0.9 |
| PS43 | 0.18 | PS44 | 0.5 |
| PS53 | 0.14 | PS54 | 0.35 |
| PS63 | 0.16 | PS64 | 0.08 |

According to the data in Table 3, it can be seen that PEI-LNP with the highest mRNA vaccine delivery efficiency had an optimal anhydride substitution type of S3-C12 alkyl chain. When S3 was used, PEI amidogen had an optimal substitution ratio of 20%.

Therefore, the present invention adopts the method for preparing PEI-LNPs used for delivering an mRNA vaccine and transfecting stem cells, wherein through a lipid PEI derivative library synthesized based on short-branched PEI with variable length and hydrophobic tail substitution ratio, short-branched PEI forms a stable complex, and plasmid DNA is delivered to stem cells, which improves effectiveness and safety of stem cell transfection.

Finally, it should be stated that the above-mentioned embodiments are only used for describing, rather than limiting, the technical solutions of the present invention. Although the present invention is described in detail by reference to the preferred embodiments, those of ordinary skill in the art should understand that they can still make modifications or equivalent substitutions to the technical solutions of the present invention, but these modifications or equivalent substitutions will not make the modified technical solutions deviate from the spirit and scope of the technical solutions of the present invention.

The invention claimed is:

1. A method of preparing polyethyleneimine-lipid nanoparticles (PEI-LNPs) for delivering an mRNA vaccine and transfecting stem cells, comprising the following specific steps:
   1) adding anhydride to a PEI solution to produce polycarboxylic acid and PEI-LNPs, wherein the anhydride is C8-C18 alkyl anhydride;
   2) dissolving the PEI-LNPs obtained in step 1, together with DPPC, DPPG, DPPE-PEG-COOH and cholesterol in chloroform to form a chloroform solution, dissolving cGAMP in a sterile water to form a cGAMP solution and then adding the cGAMP solution to the chloroform solution, and performing vacuum ultrasonication for 30 min and then vacuum evaporation to remove the chloroform and obtain a PEI-LNPs mixture;
   3) adding PBS to the PEI-LNPs mixture obtained in step 2 for hydration, and then performing ultrasonication for 20 min to obtain a liposome solution; and
   4) adding EDC/NHS to the liposome solution obtained in step 3 to perform a reaction for 15 min, then adding an mRNA to form a mixed solution, and stirring the mixed solution at a room temperature for 1 h to obtain a bionic virus nanovaccine.

2. The method according to claim 1, wherein step 2 comprises: dissolving the PEI-LNPs obtained in step 1, together with 13 µg of DPPC, 2 µg of DPPG, 2 µg of DPPE-PEG-COOH and 1 µg of cholesterol in 3 mL of chloroform to form the chloroform solution, and dissolving cGAMP in 1 mL of DNase/RNase-free water to form the cGAMP solution, and then adding the cGAMP solution to the chloroform solution, and then performing the vacuum ultrasonication for 30 min and then the vacuum evaporation to remove the chloroform and obtain the PEI-LNPs mixture;
   wherein step 3 comprises adding 2 mL of PBS to the PEI-LNPs mixture for hydration, and then performing the ultrasonication for 20 min to obtain the liposome solution; and
   wherein in step 4, EDC and NHS are each added to the liposome solution obtained in step 3 in an amount of 10 mg per mL of the liposome solution; when the mRNA is added to the liposome solution containing EDC and NHS, a volume ratio of mRNA:liposomes is 2:1.

3. The method according to claim 1, wherein in step 1, a mass ratio of PEI-LNPs:anhydride is 1:0.5.

4. The method according to claim 1, wherein in step 1, the anhydride is C12 alkyl anhydride.

5. The method according to claim 1, wherein in step 4, the mRNA vaccine has the following synthetic process:
   (1) adding an mRNA aqueous solution to such mixed solution, and performing ultrasonication for 15 min and vacuum evaporation; and
   (2) adding PBS for hydration to obtain the mRNA vaccine.

6. The method according to claim 5, wherein in step 2, the PEI-LNPs are composed of 50% of ionogenic cationic lipid DLin-MC3-DMA, 10% of DSPC, 35% of cholesterol and 5% of DPPE-PEG-COOH.

* * * * *